United States Patent
Farbrot et al.

(10) Patent No.: US 7,601,882 B2
(45) Date of Patent: Oct. 13, 2009

(54) CARRIER FOR ADDITIVE IN AN ABSORBENT ARTICLE

(75) Inventors: Anne Farbrot, Askim (SE); Ingrid Gustafsson, Asa (SE)

(73) Assignee: SCA Hygiene Products AB, Gothenburg (SE)

( * ) Notice: Subject to any disclaimer, the term of this patent is extended or adjusted under 35 U.S.C. 154(b) by 1019 days.

(21) Appl. No.: 10/800,176

(22) Filed: Mar. 12, 2004

(65) Prior Publication Data

US 2004/0181198 A1 Sep. 16, 2004

Related U.S. Application Data

(60) Provisional application No. 60/454,342, filed on Mar. 14, 2003.

(51) Int. Cl.
 A61F 13/15 (2006.01)
 A61F 13/20 (2006.01)
 A01N 25/34 (2006.01)
 A61K 31/74 (2006.01)

(52) U.S. Cl. .............. 604/368; 604/367; 604/358; 424/402; 424/78.03

(58) Field of Classification Search ......... 604/358–360, 604/367, 368, 289, 304; 602/48–51; 424/400–404, 424/443–449
See application file for complete search history.

(56) References Cited

U.S. PATENT DOCUMENTS

| | | | |
|---|---|---|---|
| 4,790,836 A | 12/1988 | Brecher | |
| 4,934,535 A * | 6/1990 | Muckenfuhs et al. | 206/494 |
| 5,635,191 A | 6/1997 | Roe et al. | |
| 5,968,025 A | 10/1999 | Roe et al. | |
| 6,168,782 B1 * | 1/2001 | Lin et al. | 424/78.03 |
| 6,187,990 B1 * | 2/2001 | Runeman et al. | 604/360 |
| 2002/0022427 A1 | 2/2002 | Curro et al. | |

FOREIGN PATENT DOCUMENTS

| | | |
|---|---|---|
| EP | 0 196 769 | 10/1986 |
| GB | 2 216 795 A * | 10/1989 |
| WO | 92/13577 | 8/1992 |
| WO | 01/47567 | 7/2001 |

OTHER PUBLICATIONS

International Preliminary Report on Patentability, PCT/SE2004/000331, Sep. 16, 2005, International Bureau of WIPO, Geneva, CH.

* cited by examiner

*Primary Examiner*—Tatyana Zalukaeva
*Assistant Examiner*—Susan Su
(74) *Attorney, Agent, or Firm*—Buchanan Ingersoll & Rooney PC

(57) ABSTRACT

The invention relates to an absorbent article, such as a sanitary towel, a panty liner, a tampon, a diaper or an incontinence pad, which article is intended to be positioned in the crotch area of a wearer and has a surface intended during use to be in contact with skin and/or mucous membranes. The article comprises at least one absorbent body (205) and a carrier (102) containing at least one additive intended to be released from the carrier (102). The carrier (102) comprises a polysiloxane gel.

18 Claims, 7 Drawing Sheets

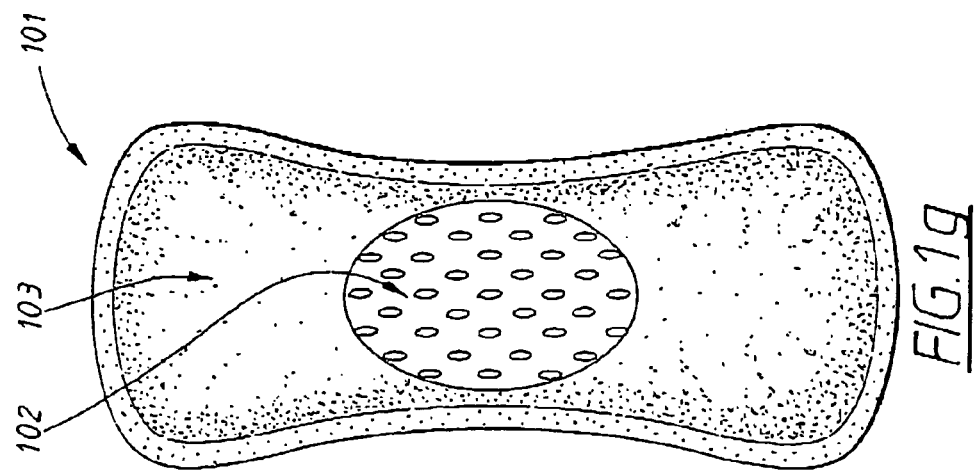
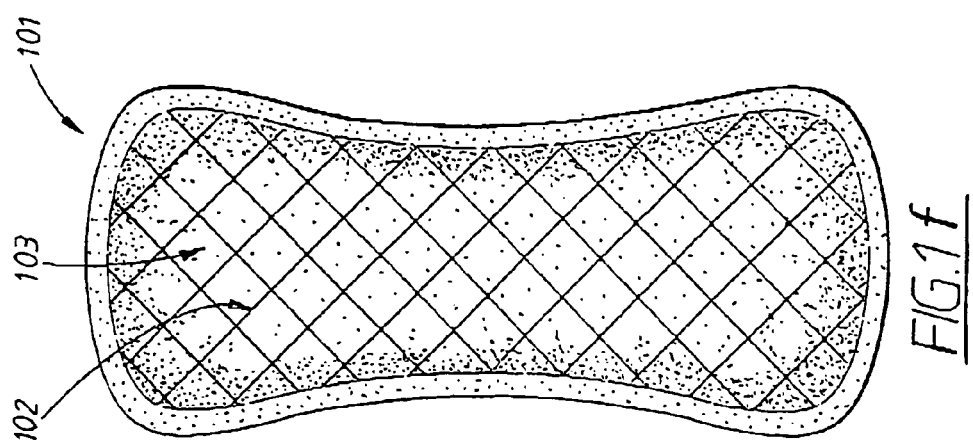

CARRIER FOR ADDITIVE IN AN ABSORBENT ARTICLE

This application is related to, and claims priority from, U.S. Provisional Application Ser. No. 60/454,342 filed on Mar. 14, 2003, the disclosure of which is expressly incorporated herein by reference.

TECHNICAL FIELD

The invention relates to an absorbent article, such as a sanitary towel, a panty liner, a tampon, a diaper or an incontinence pad, provided with at least one absorbent body and a carrier containing at least one additive which is arranged so as to be released from the carrier.

BACKGROUND ART

Providing absorbent articles with additives is common. In quite a number of cases, such additives are intended to be transferred to the skin. The additive may be, for example, an oil for lubricating and protecting the skin from drying out or an odor inhibitor which is intended to reduce unpleasant odors from menstrual fluid, urine, fecal matter and the like. It is also known to add agents such as anti-inflammatory products in order to prevent infections or strengthen the defenses of the body against them There are a number of different solutions for adding an additive to an absorbent product. One of the methods is quite simply to apply additives to the surface layer or the absorbent body. The additive can be, for example, squirted, sprayed, printed or spread onto the absorbent article in order to be released during use. In those cases where the additive cannot be added directly in the form it has in its natural state, it can be applied in the form of a solution, a dispersion or an emulsion.

In those cases where the additive is intended to be transferred to the skin, it is a disadvantage of applying the additive directly to the product that there is a risk of a large part of the additive remaining in the absorbent article and never reaching the skin. The benefit from the additive is therefore low, and the product is costly if the additive is expensive. It is also the case that if the additive is sensitive to moisture or air and is broken down or otherwise destroyed by water or oxygen, this will result in problems in storing the product. Another problem which can arise in storage is that the additive migrates as a consequence of concentration gradients, as a result of which the concentration of additive is decreased in the intended contact and reaction area.

Some of these problems can be overcome by using a carrier for the additive. In this context, carrier means a material which has the function of storing the additive until the product is used. During use, the additive is to be released and to react and/or be transferred to the skin. Some common functions of the carrier are to protect the additive during storage, to help during and to control release of additive and/or the transfer of additive to the skin of the user.

Some examples of carrier are indicated in WO 92/13577, in which publication it is proposed that a carrier with adhesive properties, such as wax or vegetable oils, is used as the carrier for an additive, in this case lactobacilli. U.S. Pat. No. 5,968,025 also discloses how wax is used as a carrier for an additive.

It is common to use various kinds of film to produce a carrier. In U.S. Pat. No. 4,790,836, use is made of a water-soluble film which is applied to the liquid-permeable surface layer. The additive is arranged between these layers and is released when the water-soluble layer becomes moist and thus dissolves.

The carrier is often located on the surface layer but can alternatively be located on the absorbent body or in an intermediate layer in the absorbent article. As far as application or addition of additive to the carrier is concerned, there are also a great many different methods. One method is quite simply to apply the additives to the carrier ply to which they bond mechanically or chemically. Another way is to manufacture a composite consisting of carrier/additive and add this onto or into the absorbent article.

Although the known carriers bring about an improvement in terms of undesirable migration in the absorbent article, these carriers still have shortcomings. For example, the problem with moisture-sensitive additives such as lactobacilli is not solved in a satisfactory manner by the previously known art.

A carrier which can release its additive under the correct conditions results in more effective utilization of the additive. Controlling the release and transfer of additives has become increasingly important. It is a complex function which requires specific properties of the carrier and is dependent on the chemical and physical properties of the additive and also on where and for what purpose the additive is to be used. There are a number of different ways of controlling and stimulating the release. If the additives are located on the surface layer, they are often released as a consequence of mechanical mechanisms, for example pressure forces and shear forces, which press the additive out of the surface or quite simply scrape it off. This process often takes place in combination with the carrier used changing viscosity with temperature. The carrier becomes more fluid, and in this way the transfer of the additive to the skin is facilitated. In such cases, the carrier is often transferred to the skin with the additive. In the patent U.S. Pat. No. 4,790,836 mentioned above, the release takes place as a consequence of a liquid-soluble layer being dissolved. In patent application U.S. 2002/022427, a surface layer breaks as a consequence of stresses applied and a duct for release of additive is opened. WO 01/47567 indicates that an additive is applied directly to fibers which are formed into a textile material, for example a nonwoven layer. The additive is released from the textile or the nonwoven layer and begins to diffuse as a consequence of movement and increased temperature.

Depending on which additive is to be released, there are different requirements for the carrier. Recently, there has been great interest in using lactobacilli or other lactic acid-producing microorganisms in sanitary towels and tampons. The lactobacilli occur naturally in the genitals of a woman and form part of the defense against infections in the genitals. By adding lactobacilli, the body's own good bacterial flora is strengthened. One of the major problems with lactobacilli in hygiene products is avoiding moisture during storage. A product which contains lactobacilli is destroyed if the water activity ($a_w$) in the product is about 0.2-0.8. Within this range, the supply of water is sufficient for metabolism to take place in the lactobacilli but too small for it to be possible for them to reproduce. The lactobacilli will die as a consequence of excessively active metabolism if they are not protected from moisture. The range indicated above corresponds to the conditions which can be expected to prevail in a product during storage in a normal indoor environment.

SUMMARY

Embodiments of the invention provide an absorbent article designed to be positioned in the crotch of a wearer and intended for absorption of bodily fluids such as menstrual fluid, urine and fecal matter. The article according to the embodiments of the invention offers an effective system for storing and releasing additives. Embodiments of the invention also aim to provide a solution to the problem of storing sensitive additives in an absorbent product as above. Embodiments of the invention are particularly suitable with regard to being capable of storing additives which are sensitive to moisture. Embodiments of the invention also contribute to reduced migration of additives into the absorbent article during storage and use and in this way make possible effective benefit from the additive. Embodiments of the invention also aim to offer controlled release of the additive during use. In accordance with the embodiments of the invention, these problems are solved by using a carrier which comprises a polysiloxane gel.

In this application, polysiloxane gel means a structure in which polysiloxanes are cross-linked and form a three-dimensional network which is swollen in a hydrophobic substance, or a substance where the greater part is hydrophobic, and forms an oil gel. Hydrophobic substances which can be used are, for example, mineral oils, such as paraffin oil, and vegetable oils, such as olive oil. Substances which for the most part are hydrophobic but have hydrophilic groups comprise, for example, mono-, di- and triglycerides, fatty acids, fatty alcohols and esters. A feature of the substance which is to be added and in this way swell the three-dimensional network is that it can interact with the network.

Using polysiloxane as a carrier for additives in diapers and sanitary towels is advantageous in a number of respects. Firstly, polysiloxane is a well-known substance which has been used previously in products with skin contact. Using polysiloxane as a carrier is therefore not associated with any direct health risks. It is also true that polysiloxane is easy to adapt as far as softness and deformation properties are concerned, primarily by controlling the degree of cross-linking. In contrast to waxes, the functioning of which as a carrier is based on the fact that they melt and are released together with the additive, the polysiloxane gel can be kept intact. A polysiloxane gel therefore stands up better to being stored at high temperatures without the additive being released. Furthermore, polysiloxane has proved to have great potential as a carrier of additives which are sensitive to and can react with moisture or air. By virtue of its hydrophobic structure, polysiloxane gel affords effective protection against the moisture of the air. As far as the protection of the carrier for oxygen-sensitive components is concerned, the gas-permeability of the polysiloxane gel can be influenced by the selection of the substance which is used in order to prepare the swollen polysiloxane gel. Something which can nevertheless be considered to be a problem with polysiloxane as a carrier on sanitary towels, diapers and similar articles is precisely its hydrophobicity and the fact that it retains its structure even after the additive has been released. Those parts of the surface layer which have been provided with polysiloxane are therefore resistant to absorbing liquid and may not allow liquid to pass through into the absorbent article.

Using polysiloxane for diapers etc. differs from using polysiloxane in, for example, a dressing. The articles covered by the present invention are intended to receive and absorb considerable quantities of liquid and other bodily discharges. There is therefore a problem with regard to retaining a very good absorption capacity at the same time as the polysiloxane gel is to be applied so that it can release a sufficient quantity of additive in the correct place. This problem can be solved by designing a polysiloxane gel structure which is sufficiently open and concentrating the polysiloxane carrier in smaller areas as described in the following illustrative embodiments. In order to provide a good absorbent capacity, the carrier should have an extent in the X-Y plane of the absorbent body which constitutes less than 30%, preferably less than 15%, and most preferably less than 5% of the area of the absorbent body in the X-Y plane. In this connection, the X-Y plane of the absorbent body means the main plane of the article when it is spread out on a plane surface. The area of the absorbent body covered by the polysiloxane carrier when the article is viewed at right angles to the X-Y plane, that is to say in the Z direction, should therefore be limited in order to minimize the effect of the polysiloxane carrier on liquid admission into the absorbent body. The polysiloxane carrier can be arranged on the surface of the absorbent body, on the surface of the liquid-permeable covering layer, or inside the absorbent body. Combinations of different positionings in the Z direction are also conceivable, it then being the projected coverage of the surface in the X-Y plane which is meant.

Polysiloxanes have a variety of very different areas of use. For example, they are used as elastomers or lubricating oils. The elastic structure of cross-linked polysiloxanes has also led to them being well suited for use in sticking plasters and other dressings. They are moreover used as heat-insulating panels on the underside of space shuttles and also in hair care products or baby lotion.

Polysiloxanes are often referred to somewhat incorrectly as silicones because it was first assumed that the polysiloxane chain consisted of silicon. However, the actual structure consists of alternating silicon (Si) and oxygen (O) atoms with different substituents (R) bonded to the silicon atoms (see below). "Silicones" nevertheless remains as the commonest trivial name for polysiloxanes.

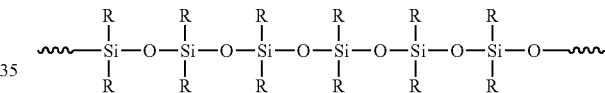

The most common substituents (R) are methylene groups, polydimethylsiloxane (PDMS) then being formed. The R groups can consist of on the whole any organic or inorganic substituent. The substituents influence the physical and chemical properties of the polysiloxane, and different substituents can be used in order, for example, to modify the elasticity and the adhesive capacity of the polysiloxane. Apart from PDMS gels, it is of particular interest to use gels in which the methylene groups have been replaced by hydrogen, alkyl, phenyl or other organofunctional groups as the carrier. The end groups in the polysiloxane chain also play a role with regard to the properties the polysiloxane has, and of these silanol, vinyl, alkoxy and hydrogen are of particular interest in the present area of use.

The properties of the polysiloxanes are also determined to a great extent by the degree of cross-linking. Silicone oils, for example, consist of polysiloxanes which are not cross-linked, that is to say individual polysiloxane chains with specific molecular weight, whereas sticking plasters, for example, comprise cross-linked polysiloxane chains with infinite molecular weight. The polysiloxanes can be hardened into a three-dimensional network by radical polymerization or via catalyzed hydrosilanization. The three-dimensional network has an infinite molecular weight and can in the dry (unswollen) form be called a silicone matrix. As mentioned previously, the matrix can swell in at least partly hydrophobic additives (for example mineral or vegetable oils). In this connection, an oil gel is formed. An oil gel can also be formed by virtue of the cross-linking reaction between the siloxane chains being carried out in the presence of at least partly hydrophobic additives. Depending on which additive is to be used in the carrier, it can be added either in connection with the oil being added or afterwards. By using different cross-linking reactions and allowing these to continue for different lengths of time, the degree of cross-linking and associated properties, for example the mesh size of the cross-linked network, can be controlled and modified. The degree of cross-linking is adapted according to the additives for which the polysiloxane gel is to be used as a carrier, so that optimum interaction is achieved between the matrix and the additive which is to be released. The meshes are to be sufficiently large for it to be possible for the additive to be released from the gel but at the same time so small that the network can retain the hydrophobic agent with additive during storage. The mesh size in the three-dimensional network is therefore important for the rate of release of the additive.

By adapting the polysiloxanes in terms of the length of the main chain, selection of substituents and different kinds of end groups, control of the cross-linking reaction and selection of hydrophobic liquid for swelling the three-dimensional network, the properties of the gel can be determined. The relationship between the polarity of the cross-linked polysiloxane network and the polarity of the liquid which is used in order to swell the gel is of great importance for the release rate of the additive. Depending on which type of additive is to be released, and the chemical and physical properties the additive has, the gel can be formed and tailored for specific requirements. An especially important property to take into consideration when the carrier is being designed is the water-solubility of the additive, that is to say whether the additive is hydrophobic, hydrophilic or amphiphilic.

The release mechanism should be adapted to the purpose of the additive. For example, cooling agent can react to temperature. Oils which are to lubricate the skin can react to great shear forces between the article and the skin, and odor inhibitors can react to absorption of liquid. By modifying the properties of the gel, it can be adapted especially for the additive to be used.

There are number of different types of additive which are appropriate for use together with a siloxane gel carrier in accordance with the invention. Cells/bacteria or similar microorganisms are expected to have great potential in future hygiene articles. These are intended primarily to be used in order to strengthen the natural defenses of the body against infections, but it is also conceivable for them to be used as, for example, odor inhibitors. Lotions or oils can be added as skin care agents, as can vegetable extract such as Aloe Vera or substances like minerals, vitamins or other skin care agents. The additive concerned here can be identical with the liquid used in order to swell the three-dimensional polysiloxane network. The same substance therefore performs both the function of active substance and that of gel-former together with the polysiloxane network.

By using a polysiloxane carrier, a considerable improvement is achieved in the storage of water-sensitive additives as polysiloxane provides an effective moisture barrier during storage. The polysiloxane gel can also function as protection against oxygen in the air by virtue of the fact that the polysiloxane is swollen in a hydrophobic liquid which reduces the air-permeability. Another advantage of using a polysiloxane gel as a carrier is that it is relatively temperature-insensitive and can preserve the additive at temperatures which lie well above normal room temperature, which are not infrequent during the transport or storage of absorbent articles. The polysiloxane gel is also elastic and therefore resistant to mechanical breaking or stretching forces. Furthermore, its elastic properties can be utilized in order to replace or supplement other elastic in the article and in this way achieve the desired elastic properties in the article.

DESCRIPTION OF FIGURES

The invention will be described in greater detail below with reference to the figures shown in the accompanying drawings, in which:

FIGS. 1a-g show a sanitary towel with a carrier according to the invention applied in different patterns to the liquid-permeable surface layer of the towel;

DESCRIPTION OF EMBODIMENTS

FIGS. 1a-g show various embodiments of how polysiloxane gel can be applied. In the illustrations, the layout of the polysiloxane gel carrier 102 is exemplified on the liquid-permeable surface layer of a sanitary towel 101. In positioning the carrier, the aim is for it to be positioned in such a way that it disrupts the absorption as little as possible at the same time as the carrier is to release its additive, or its additives, in an effective manner. The purpose of the additive plays an important role in how the polysiloxane gel is to be arranged on the absorbent article, as do the kinds of additive to be absorbed. The carrier with additive can either be applied to the surface layer before the latter is attached to the towel or be applied to the surface layer after this has been attached to the towel.

Figure 1C:
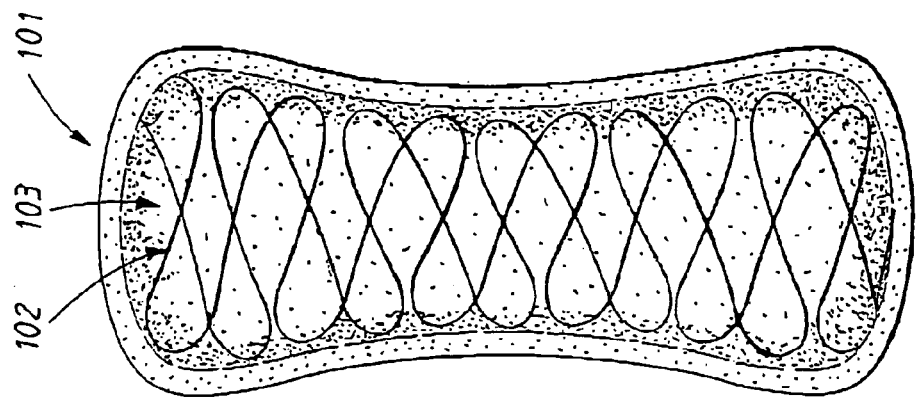
Figure 1B:
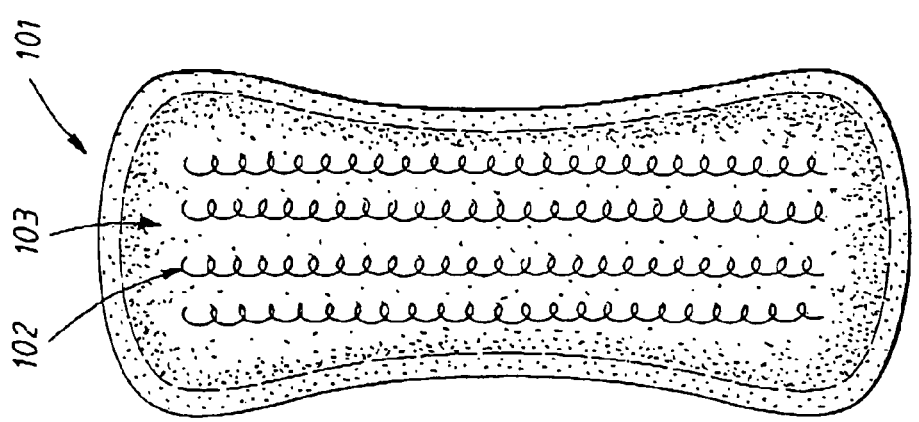
Figure 1A:
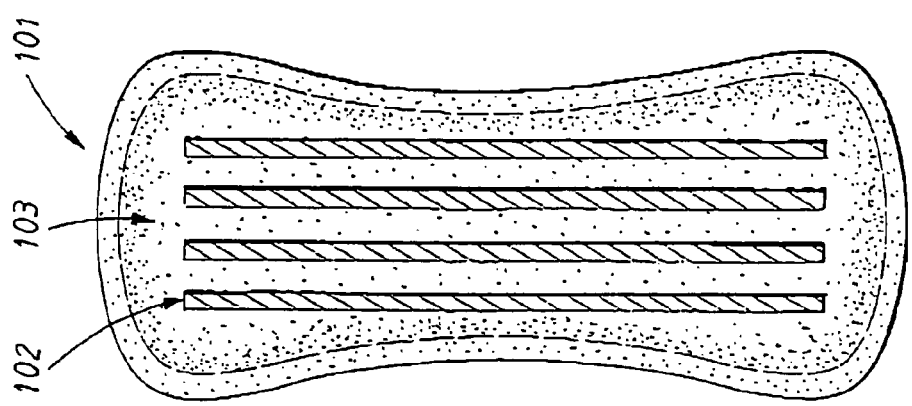

FIG. 1a shows a sanitary towel 101 with a carrier 102 in the form of four polysiloxane strands laid out on the surface layer 103. The number of strands can of course be greater or smaller than shown in the figure. The strands are, say, from 5 to 20 cm long, preferably about 10 cm long, and from 0.2 to 2 cm wide, preferably about 0.5 cm wide. The thickness is, say, less than 3 mm. Dimensioning depends of course on the size of the absorbent article, and which additive is to be released.

FIG. 1b shows a sanitary towel 101 with a carrier 102 in the form of spirals or waves formed by thin strands applied to the surface layer 103. The strands can be round with a diameter of up to 3 mm or flattened with an oval cross section.

FIG. 1c shows a sanitary towel 101 with a carrier 102 in the form of long, fiber-like threads which are distributed uniformly on the surface layer 103. Producing the carrier 102 in the form of long, fiber-like threads can be especially advantageous if the carrier 102 is to be combined with one of the layers making up the towel, for example the surface layer 103. It is therefore possible to envisage a nonwoven made partly from polysiloxane fibers. In the case of such intermixing, the elastic properties of the polysiloxane can also be utilized for achieving the desired material properties in the composite material formed.

Figure 1D:
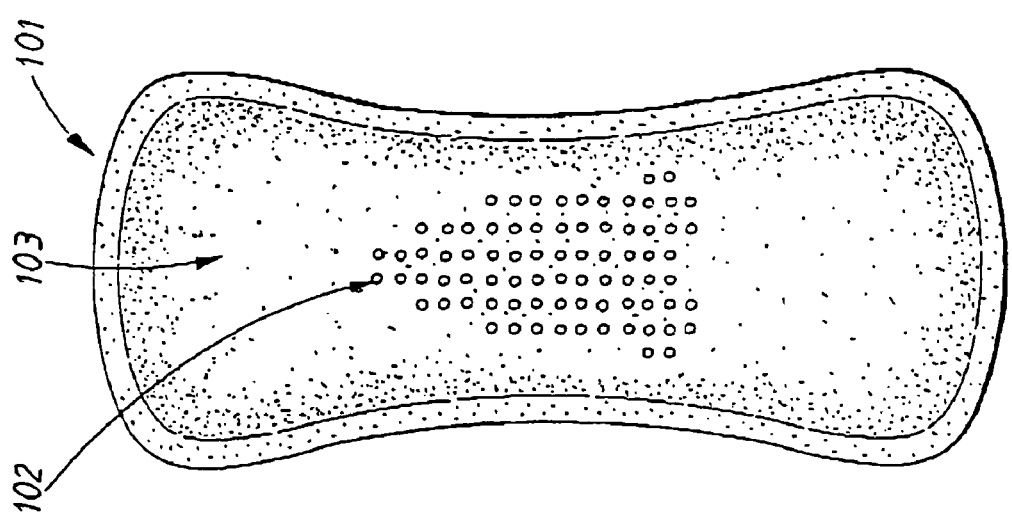
Figure 1E:
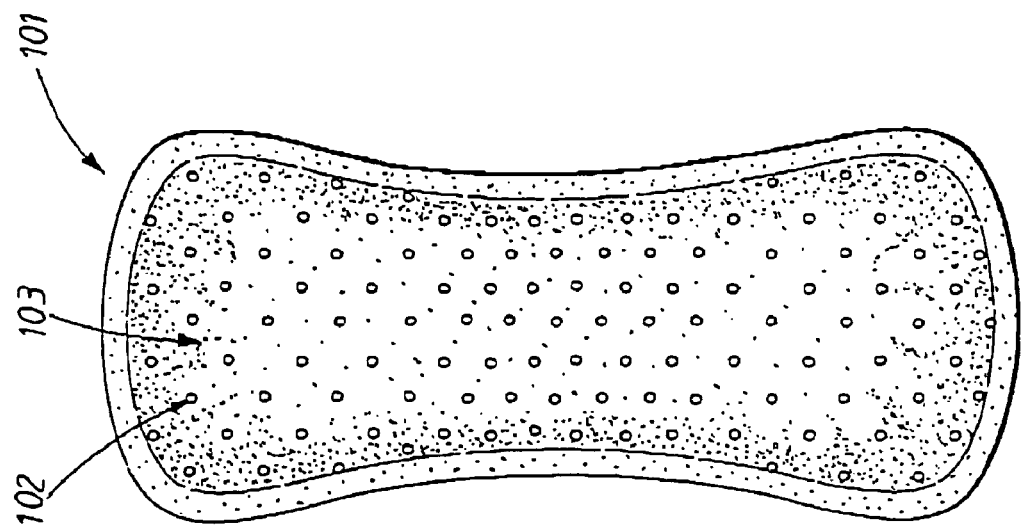

FIGS. 1d and 1e show a sanitary towel 101 with a carrier 102 applied to the surface layer 103 in the form of a discontinuous pattern of dots. It can be seen from FIG. 1e that the entire surface layer is covered by uniformly distributed small dots. These dots could alternatively be concentrated in certain parts of the surface layer. In FIG. 1d, the carrier 102 is applied to the surface layer 103 in the form of slightly larger dots, and a greater part of the surface layer of the towel 101 is covered in the areas where it is considered most important to apply additive. It is also conceivable for the dots to be uniformly distributed over the entire surface. The dots can of course vary in both size and shape. The size or shape the dots have is not particularly critical for the invention, but their area is usually from 0.01 cm² to 1 cm².

FIG. 1f shows a sanitary towel 101 with a carrier 102 which is applied to the surface layer 103 in the form of a net. FIG. 1f shows the net extending over the whole surface layer of the towel 101, but it is of course alternatively conceivable for only parts of the surface to be covered by the net.

FIG. 1g shows a sanitary towel 101 with a carrier 102 which is applied to the surface layer 103 in the form of a perforated gel. FIG. 1g shows the perforated gel covering only part of the surface layer of the towel, but it is of course alternatively conceivable for the gel to extend over the entire surface layer.

FIGS. 1a-g exemplify how the carrier can be applied to the surface layer of a sanitary towel. It is clear that these different ways of applying the carrier can also be used for panty liners, diapers, incontinence pads or the like. Similar patterns can also be used for tampons.

It is of course conceivable to use combinations of these different shapes and versions of the carrier in one and the same product, for example a discontinuous strand consisting of dots, a perforated gel together with dots, or patterns of dots in different shapes and sizes.

Figure 2:
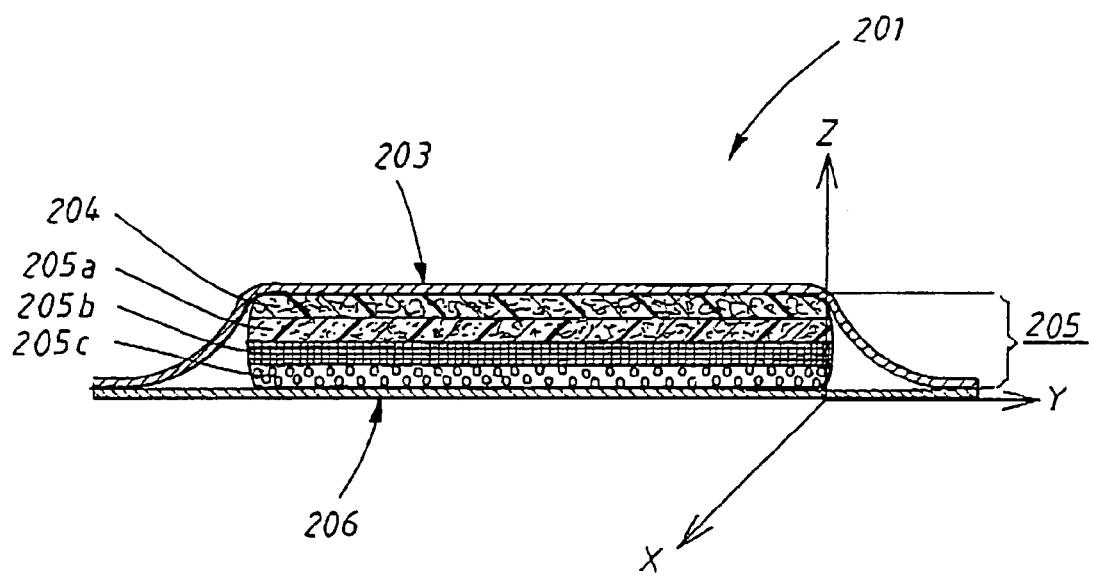
FIG. 2 shows an absorbent article in cross section.

FIG. 2 shows an absorbent article 201 in cross section. The absorbent article 201 consists of a liquid-permeable surface layer 203, a liquid-impermeable backing layer 206 and an absorbent layer 205 therebetween. It is also common for there to be a receiving and spreading layer 204 in order to take up and spread liquid over the absorption layer 205. Such a receiving and spreading layer 204 is usually positioned between the surface layer 203 and the absorption layer 205 but can be positioned on the surface layer 203 or be integrated into the surface layer 203 or the absorption layer 205. The layers which have been described can in turn consist of various plies; for example, the absorption layer 205 can be divided into receiving plies 205a, distributing plies 205b and retention plies 205c.

It is of course the case that the carrier 102 according to the embodiments 1a-g shown can be positioned between some of the layers 203-206 or plies which make up the absorbent article 201 instead of on the surface layer 203. Another possibility is to intermix the carrier 102 with one or some of the layers 203-206 so that these consist of a composite material containing polysiloxane. Depending on the intended function of the additive, different ways of positioning the carrier 102 are suitable in different ways. If the additive is intended to act on or be transferred to skin or mucous membranes, it is in most cases advantageous to position the carrier 102 so that it has direct contact with the skin or the mucous membranes. If the intention is for the additive to react with the absorbed liquid, the carrier 102 should be positioned so that it comes into contact with a large part of the liquid. This can be achieved by concentrating the carrier 102 in the part which receives the liquid in the surface layer 203 or the receiving and spreading layer 204. This can, however, result in certain disadvantages because the polysiloxane gel represents inert points with regard to absorption. By positioning the carrier 102 below the receiving and spreading layer 204 and having the carrier 102 distributed uniformly over the absorption layer 205, the additive which is released from the carrier 102 can come into contact and react with a large part of the absorbed liquid. The carrier 102 is to be positioned in such a way, with regard to the X-Y plane and in the Z direction, that the additive is utilized as well as possible. Depending on the function of the additive, the most suitable places for positioning the carrier 102 vary. It is of course conceivable to position one or more different carriers in different places in one and the same product, both in the plane of the product and in its depth direction. The carrier or the carriers can then be designed to release the same additive or different additives. It is also possible to arrange carrier with a different concentration of additive within different areas.

FIGS. 3a-e show various places which are appropriate for application of the carrier.

Figure 3B:
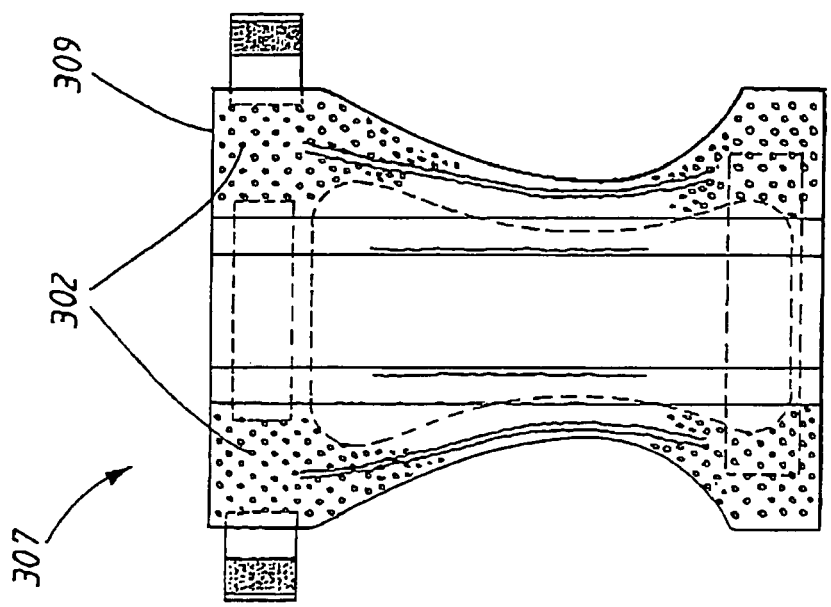
FIGS. 3a-e show carriers containing additive arranged in different places on absorbent articles.
Figure 3A:
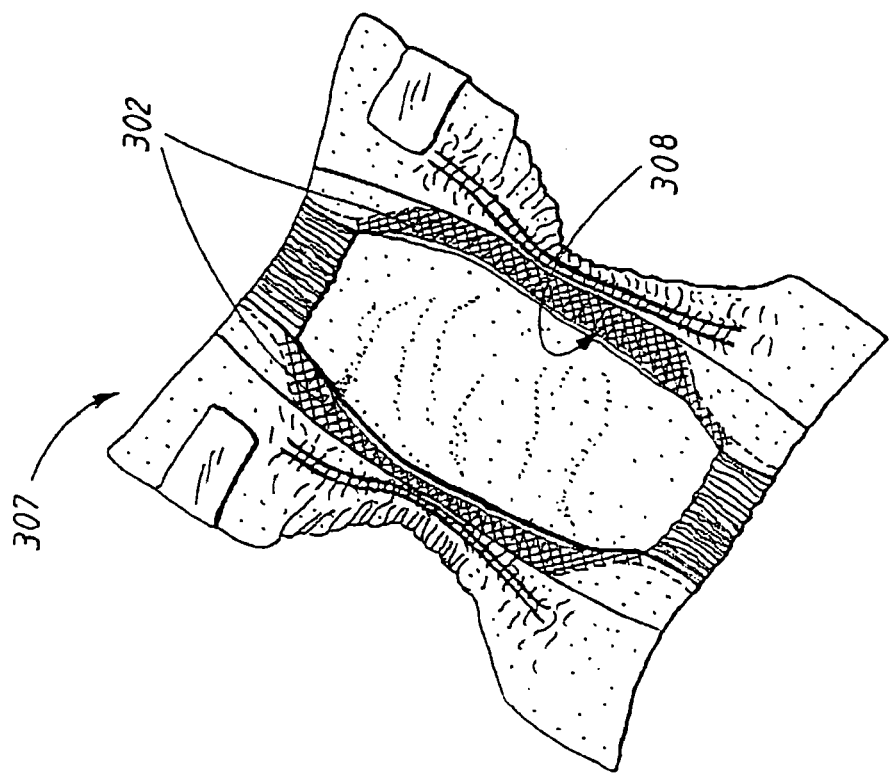

FIG. 3a shows a diaper 307 with a carrier 302 which is attached to or adjacent to an elastic, upright barrier 308 which protects against side leakage. A likely additive in this illustrative embodiment is some kind of oil or skin care agent which helps counteract chafing.

FIG. 3b shows a diaper 307 with a carrier 302 which is attached to a side panel 309 on the side which faces the wearer. In this case too, oil or skin care agent which counteracts chafing is a likely additive.

Figure 3E:
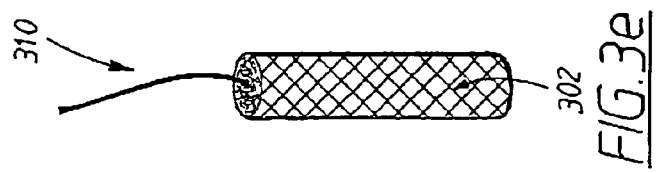
Figure 3D:
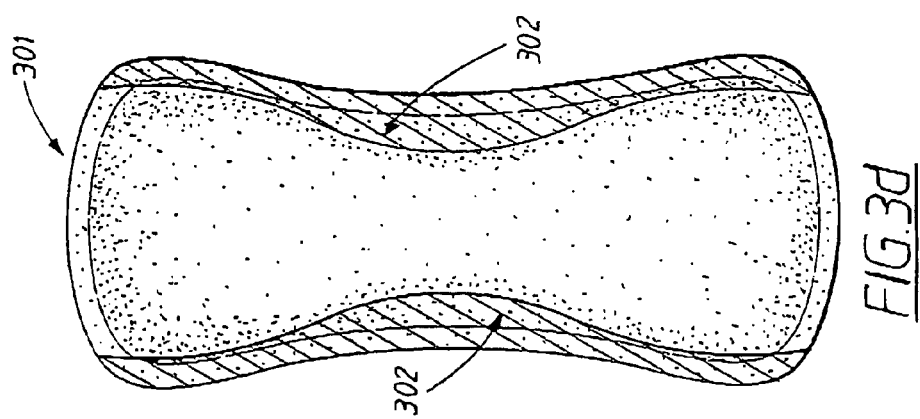
Figure 3C:
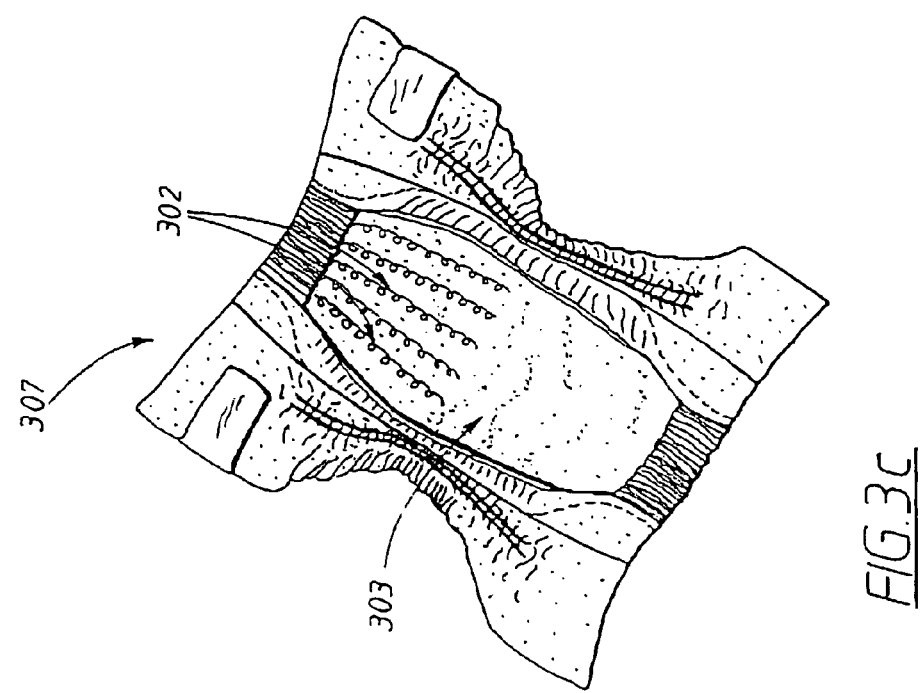

FIG. 3c shows a diaper 307 which has been provided with carrier 302 on the surface layer 303, from the central portion (the crotch) backwards. In this case, the most likely additive is some kind of skin care agent to counteract skin irritation.

FIG. 3d shows a sanitary towel 301 with a carrier 302 located on the edge of the towel 301.

FIG. 3e shows a tampon 310 which has been provided with a carrier 302 in the form of a net-like structure. It is assumed to be especially advantageous to use such a structure for a tampon 310 because the net will be subjected to pressure forces when liquid is absorbed and the tampon 310 swells, as a result of which release of the additive is improved.

It is of course possible to envisage other similar absorbent articles such as light incontinence pads for women or men, the pads being provided with polysiloxane gel as a carrier for an additive.

Figures 4A, 4B:
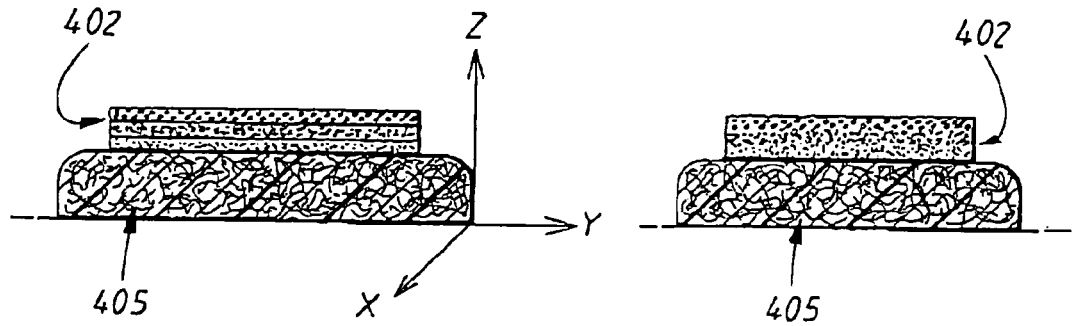
FIG. 4 shows a carrier in cross section, the degree of cross-linking of which varies in the Z direction, that is to say in the thickness direction.

FIG. 4 is a diagrammatic illustration which shows a carrier 402 in which the degree of cross-linking varies in the Z direction, that is to say in the thickness direction. This variation is intended to guide the release in the direction from the absorbent body so that diffusion down into the absorbent body 405 is reduced. The mesh size of the gel therefore increases in the Z direction towards the contact surface with the wearer. The intention is to direct the release of substance so that it can be released only in one direction. In a case where an additive is to be released from, for example, a sanitary towel and transferred to the wearer, the polysiloxane gel is cross-linked as is shown in FIG. 4. The mesh size gradient can either be continuous as shown in FIG. 4b or consist of different plies with different mesh sizes as shown in FIG. 4a.

Figure 5:
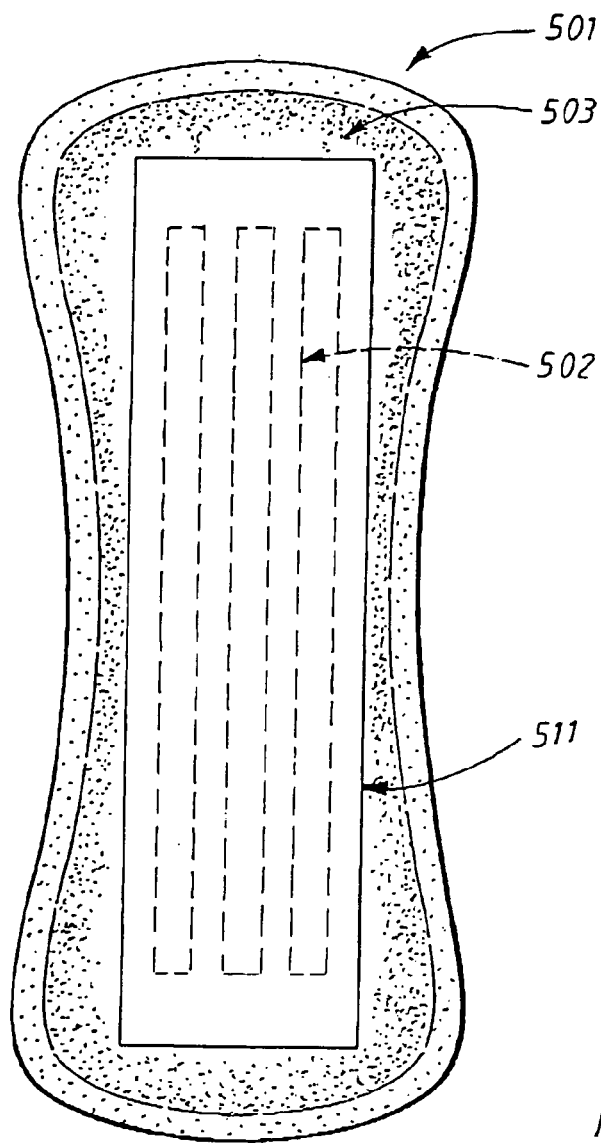
FIG. 5 shows an absorbent article with a carrier on the surface layer, which is provided with a protective layer.

FIG. 5 shows a sanitary towel 501 with a carrier 502 on the surface layer 503, the carrier being provided with a protective layer 511. The said protective layer is intended to prevent migration of additives during storage and transport of the towel and is removed before use in order to make release of additives possible.

The invention claimed is:

1. An absorbent article, which article is intended to be positioned in the crotch area of a wearer and has a surface intended during use to be in contact with skin and/or mucous membranes and which comprises at least one absorbent body and a carrier containing at least one additive intended to be released from the carrier, wherein the carrier comprises a polysiloxane gel, wherein the polysiloxane gel is a structure in which polysiloxanes are cross-linked and form a three-dimensional network which is swollen in a hydrophobic substance, or a substance where the greater part is hydrophobic, and forms an oil gel.

2. Absorbent article according to claim 1, wherein the carrier has an extent in the X-Y plane of the absorbent body which constitutes less than 30% of the area of the absorbent body in the X-Y plane.

3. Absorbent article according to claim 2, wherein the carrier has an extent in the X-Y plane of the absorbent body which constitutes less than 15% of the area of the absorbent body in the X-Y plane.

4. Absorbent article according to claim 3, wherein the carrier has an extent in the X-Y plane of the absorbent body which constitutes less than 5% of the area of the absorbent body in the X-Y plane.

5. Absorbent article according to claim 1, wherein the additive to be released comprises lactobacilli.

6. Absorbent article according to claim 1, wherein the additive to be released comprises at least one active substance selected from: oil, lotion, anti-chafing agent, odor inhibitor, cooling agent or vegetable extract.

7. Absorbent article according to claim 1, wherein the additive also constitutes an agent for swelling the three-dimensional polysiloxane network.

8. Absorbent article according to claim 1, wherein the polysiloxane gel is loosely cross-linked.

9. Absorbent article according to claim 8, wherein the polysiloxane gel is cross-linked so that the meshes have a size of at least 1 micrometer.

10. Absorbent article according to claim 9, wherein the degree of cross-linking of the polysiloxane gel decreases, and thus its mesh size increases, in the direction towards that surface of the gel which is intended to release the additive.

11. Absorbent article according to claim 1, wherein the polysiloxane gel is applied to the absorbent article in the form of a net, a perforated gel, a latticed pattern or strands.

12. Absorbent article according to claim 1, wherein the release of additive by the polysiloxane gel is activated by diffusion, pressure, heat, movement, liquid or moisture, friction forces, shear forces or a combination of these.

13. Absorbent article according to claim 1, wherein that surface of the polysiloxane gel which faces the skin during use is covered by a detachable protective layer.

14. Absorbent article according to claim 1, wherein the polysiloxane gel is mixed with a glue.

15. Absorbent article according to claim 1, wherein the polysiloxane gel is intermixed with the absorbent body and/or with a surface layer or a spreading layer in the absorbent article.

16. A method of providing an additive to an absorbent article comprising providing a polysiloxane gel with an additive and attaching the polysiloxane gel to an absorbent article, which article is intended to be positioned in the crotch area of a wearer, and wherein the additive is arranged so as to be released from the polysiloxane gel during use of the absorbent article,
wherein the polysiloxane gel is a structure in which polysiloxanes are cross-linked and form a three-dimensional network which is swollen in a hydrophobic substance, or a substance where the greater part is hydrophobic, and forms an oil gel.

17. Absorbent article according to claim 2, wherein the additive to be released comprises lactobacilli.

18. Absorbent article according to claim 1, comprising a sanitary towel, panty liners, a tampon or an incontinence pad.

* * * * *

UNITED STATES PATENT AND TRADEMARK OFFICE
CERTIFICATE OF CORRECTION

PATENT NO.      : 7,601,882 B2
APPLICATION NO. : 10/800176
DATED           : October 13, 2009
INVENTOR(S)     : Farbrot et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1138 days.

Signed and Sealed this

Fifth Day of October, 2010

David J. Kappos
*Director of the United States Patent and Trademark Office*